US00PP15842P2

(12) United States Plant Patent
Fruehwirth

(10) Patent No.: US PP15,842 P2
(45) Date of Patent: Jul. 5, 2005

(54) ***POINSETTIA* PLANT NAMED 'ECKALLYN'**

(50) Latin Name: *Euphorbia pulcherrima*
Varietal Denomination: Eckallyn

(75) Inventor: Franz Fruehwirth, Encinitas, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 10/859,516

(22) Filed: Jun. 1, 2004

(51) Int. Cl.[7] ..... A01H 5/00
(52) U.S. Cl. ..... Plt./306
(58) Field of Search ..... Plt./306

(56) References Cited

PUBLICATIONS

UPOV–ROM GTITM, Plant Variety Database, 2004/04, GTI Jouve Retrieval Software, Citation for *Euphorbia* 'Eckallyn'.*

* cited by examiner

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Poinsettia* plant named 'Eckallyn', characterized by its ball-shaped inflorescences with recurved dark pink-colored flower bracts; recurved dark green-colored leaves; uniform plant habit; and excellent postproduction longevity.

1 Drawing Sheet

Botanical classification/cultivar designation: *Euphorbia pulcherrima* Willd. cultivar Eckallyn.

BACKGROUND OF THE INVENTION

The present Invention relates to a new and distinct cultivar of *Poinsettia* plant, botanically known as *Euphorbia pulcherrima* Willd., and hereinafter referred to by the name 'Eckallyn'.

The new *Poinsettia* a product of a planned breeding program conducted by the Inventor in Encinitas, Calif. The objective of the breeding program is to create new *Poinsettia* cultivars having strong stems, reflexed flower bracts with desirable colors, uniform plant habit and excellent post-production longevity.

The new *Poinsettia* is a naturally-occurring branch mutation of the *Euphorbia pulcherrima* Willd. cultivar Winred, disclosed in U.S. Plant Pat. No. 12,042. The new *Poinsettia* was discovered and selected by the Inventor within a population of plants of the cultivar Winred in a controlled environment in Encinitas, Calif. The selection of this plant was based on its strong stems and reflexed dark pink-colored flower bracts.

Asexual reproduction of the new *Poinsettia* by terminal cuttings propagated in a controlled environment in Encinitas, Calif., since 1999, has shown that the unique features of this new *Poinsettia* are stable and reproduced true to type in successive generations of asexual reproduction.

BRIEF SUMMARY OF THE INVENTION

The following traits have been repeatedly observed and are determined to be the unique characteristics of 'Eckallyn'. These characteristics in combination distinguish 'Eckallyn' as a new and distinct cultivar:

1. Ball-shaped inflorescences with recurved pink-colored flower bracts.
2. Recurved dark green-colored leaves.
3. Uniform plant habit.

4. Strong erect stems.
5. Response time about 9.5 weeks.
6. Excellent post-production longevity.

Plants of the new *Poinsettia* are most similar to the parent, the cultivar Winred. Plants of the new *Poinsettia* differ primarily from plants of the parent in flower bract coloration as plants of the cultivar Winred have red-colored flower bracts.

Plants of the new *Poinsettia* can be compared to plants of the cultivar Eckaddis, disclosed in U.S. Plant Pat. No. 12,782. In side-by-side comparisons conducted in Encinitas, Calif., plants of the new *Poinsettia* differed from plants of the cultivar Eckaddis in the following characteristics:

1. Plants of the new *Poinsettia* were taller than plants of the cultivar Eckaddis.
2. Plants of the new *Poinsettia* flowered about three or four days later than plants of the cultivar Eckaddis.
3. Plants of the new *Poinsettia* had smaller flower bracts than plants of the cultivar Eckaddis.

BRIEF DESCRIPTION OF THE PHOTOGRAPHS

The accompanying colored photographs illustrate the overall appearance of the new *Poinsettia*, showing the colors as true as it is reasonably possible to obtain in colored reproductions of this type. Colors in the photographs may differ slightly from the color values cited in the detailed botanical description which accurately describe the colors of the new *Poinsettia*.

The photograph at the top of the sheet comprises a side perspective view of a typical flowering plant of 'Eckallyn'.

The photograph at bottom of the sheet is a top perspective view of a typical flowering plant of 'Eckallyn'.

DETAILED BOTANICAL DESCRIPTION

The new *Poinsettia* has not been observed under all possible environmental conditions. The phenotype may vary somewhat with variations in environment such as temperature, daylength and light intensity, without, however, any variance in genotype.

The aforementioned photographs, following observations and averaged measurements describe plants grown in Encinitas, Calif. during the autumn and winter under commercial practice in a polyethylene-covered greenhouse with day temperatures about 24° C., night temperatures about 19° C., and light levels about 4,000 foot-candles. Single plants were grown in 16.5-cm pots with three plants per plant and were grown as single stems. Plants were flowered under natural season short day/long night conditions. Plants were about 18 weeks from unrooted cuttings when the photographs and the detailed botanical description were taken.

In the following description, color references are made to The Royal Horticultural Society Colour Chart, 1995 Edition, except where general terms of ordinary dictionary significance are used.

Botanical classification: *Euphorbia pulcherrima* Willd. cultivar Eckallyn.

Parentage: Naturally-occurring branch mutation of *Euphorbia pulcherrima* Willd. cultivar Winred, disclosed in U.S. Plant Pat. No. 12,042.

Propagation:

*Type cutting.*—Terminal cuttings.

*Time to initiate roots.*—About ten days at 20 to 22° C.

*Time to develop roots.*—About four weeks at 24° C.

*Root description.*—Thick, fibrous and freely-branching.

Plant description:

*Plant form.*—Narrow inverted triangle; strong and erect stems.

*Growth habit.*—Upright and uniform plant habit. Moderately vigorous.

*Plant height.*—About 35 cm.

*Plant diameter or spread.*—About 15 cm.

*Branch description.*—Quantity: Grown as a single stem, all laterals are removed and only the terminal branch develops. Length: About 30 cm. Diameter: About 1 cm. Internode length: About 1.75 cm. Strength: Strong, stiff. Texture: Smooth; glabrous. Color: 144B.

*Foliage description.*—Arrangement: Alternate, single. Length: About 10 cm. Width: About 8.2 cm. Shape: Roughly cordate. Apex. Acuminate; twisted. Base: Rounded to cordate. Margin: Entire. Venation pattern: Pinnate. Texture, upper and lower surfaces: Glabrous; rugose. Orientation: Recurved. Color: Developing and fully expanded foliage, upper surface: Darker than 147A. Developing and fully expanded foliage, lower surface: More gray than 147B. Venation, upper surface: 147C. Venation, lower surface: 147C to 147D. Petiole: Length: About 3.9 cm. Diameter: About 2.5 mm. Texture, upper and lower surfaces: Smooth; glabrous. Color: 146D.

Inflorescence description:

*Inflorescence type and habit.*—Inflorescences are compound corymbs of cyathia with colored flower bracts subtending the cyathia. One inflorescence per terminal branch. Flower bracts recurved, inflorescences ball-shaped. Flowers are not fragrant. Flowers persistent.

*Natural flowering season.*—Autumn/winter in Northern Hemisphere. Flower initiation and development is induced under long nyctoperiod conditions. Response time, about 9.5 weeks; natural season flower maturity date is early December for plants grown in Encinitas, Calif.

*Post-production longevity.*—Plants of the new *Poinsettia* maintain good substance and bract color for about four weeks under interior conditions.

*Inflorescence size.*—Diameter: About 12 cm. Height (depth): About 7.5 cm.

*Flower bracts.*—Quantity per inflorescence: About 26. Length, largest bracts: About 6.5 cm. Width, largest bracts: About 5 cm. Shape: Cordate to elliptic. Apex. Acuminate, curled. Base: Obtuse. Margin: Entire; slightly sinuate. Texture, upper and lower surfaces: Glabrous; velvety; rugose. Orientation: Recurved. Venation pattern: Pinnate. Color: Developing or transitional bracts, upper surface: 52A to 52B. Developing or transitional bracts, lower surface: 52B. Fully developed bracts, upper surface: 52B. Fully developed bracts, lower surface: 51B. Venation, upper and lower surfaces: Similar to flower bract color. Bract petiole: Length: About 1.5 cm. Diameter: About 3 mm. Texture, upper and lower surfaces: Smooth; glabrous. Color: 59B.

*Cyathia.*—Quantity: About ten per corymb. Diameter of cyathia cluster: About 2 cm by 2.5 cm. Length: About 1 cm. Width: About 7 mm. Shape: Ovoid. Color, immature: 144B. Color, mature: 144C. Peduncle: Length: About 3 mm. Diameter: About 2 mm. Strength: Strong. Aspect: Mostly upright. Texture: Smooth; glabrous. Color: 144C. Stamens: Quantity per cyathium: About 15 to 20. Anther shape: Oval. Anther length: Less than 1 mm. Anther color: 162A. Amount of pollen: Scarce. Pollen color: 7A. Pistils: None observed. Nectaries: Quantity per cyathium: One. Size: About 4 mm by 7 mm. Color: 23A.

Disease/pest resistance: Resistance to pathogens and pests common to *Poinsettias* has not been observed on plants grown under commercial conditions.

It is claimed:

1. A new and distinct cultivar of *Poinsettia* plant named 'Eckallyn', as illustrated and described.

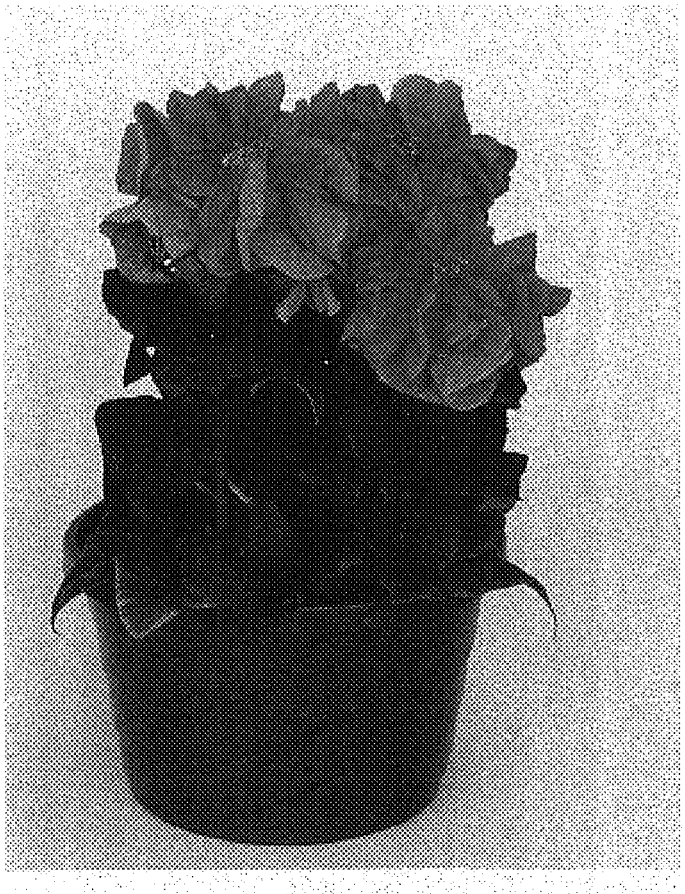
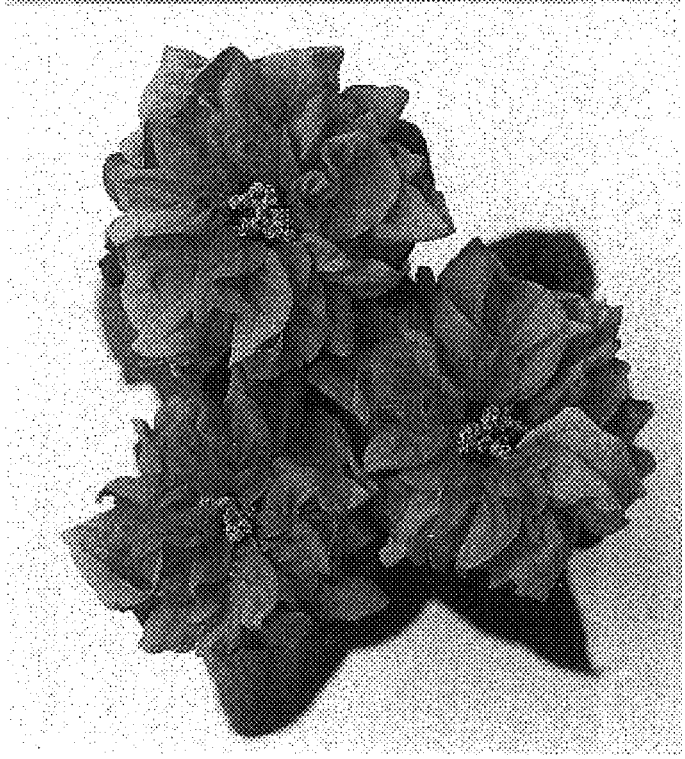

* * * * *